(12) United States Patent
West et al.

(10) Patent No.: US 9,364,169 B2
(45) Date of Patent: Jun. 14, 2016

(54) APPARATUS METHOD AND SYSTEM FOR MEASURING STRAIN IN BIOLOGICAL TISSUE

(71) Applicant: Brigham Young University, Provo, UT (US)

(72) Inventors: Christopher R. West, Sandy, UT (US); Anton E. Bowden, Lindon, UT (US)

(73) Assignee: Brigham Young University, Provo, UT (US)

(*) Notice: Subject to any disclaimer, the term of this patent is extended or adjusted under 35 U.S.C. 154(b) by 248 days.

(21) Appl. No.: 13/769,089

(22) Filed: Feb. 15, 2013

(65) Prior Publication Data

US 2013/0211279 A1 Aug. 15, 2013

Related U.S. Application Data

(60) Provisional application No. 61/633,659, filed on Feb. 15, 2012.

(51) Int. Cl.
*A61B 5/11* (2006.01)
*A61B 5/053* (2006.01)
*A61B 5/00* (2006.01)

(52) U.S. Cl.
CPC ............. *A61B 5/1126* (2013.01); *A61B 5/0004* (2013.01); *A61B 5/053* (2013.01);
(Continued)

(58) Field of Classification Search
CPC .... A61B 5/053; A61B 5/1126; A61B 5/4523; A61B 5/4533; A61B 2562/0209; A61B 5/0492
USPC ................. 600/372, 373, 382, 386, 393, 587; 702/42, 43, 57, 64, 65; 607/115, 116, 607/148
See application file for complete search history.

(56) References Cited

U.S. PATENT DOCUMENTS 4,294,015 A * 10/1981 Drouin et al. .................... 73/831
5,056,530 A * 10/1991 Butler et al. .................. 600/587

(Continued)

OTHER PUBLICATIONS

Onaral, B. and Bronzino, J. D. "Future Directions: Biomedical Signal Processing and Networked Multimedia Communications" Biomedical Engineering Handbook (3rd Edition. 2006). Retrieved from <http://app.knovel.com/hotlink/toc/id:kpBEHBEFE4/biomedical-engineering/biomedical-engineering> on May 5, 2015.*
Chen, C. T., et al. "Transient and cyclic responses of strain-generated potential in rabbit patellar tendon are frequency and pH dependent." Journal of biomechanical engineering 122.5 (2000): 465-470.*

(Continued)

*Primary Examiner* — Devin Henson
*Assistant Examiner* — David J McCrosky

(57) ABSTRACT

An apparatus for in-situ sensing of longitudinal and transverse strain in biological tissue (e.g. tendons and ligaments) includes a set of sensing electrodes that contact biological tissue and enable measurement of an electrical property of the biological tissue along two or more directions. The apparatus may also include a sensing module that senses the electrical property of the biological tissue along the two or more directions to provide multi-directional measurements that are captured by a logging module. The apparatus may also include a transmission module that transmits the captured measurements to a data analysis workstation or the like. The data analysis workstation may include a strain estimation module that receives the multi-directional measurement and estimates a longitudinal strain and a transverse strain therefrom. A corresponding system and method for in-situ sensing of longitudinal and transverse strain in biological tissue is also presented.

17 Claims, 4 Drawing Sheets

(52) U.S. Cl.
CPC ............ *A61B 5/0538* (2013.01); *A61B 5/4523* (2013.01); *A61B 5/4533* (2013.01); *A61B 5/7278* (2013.01); *A61B 2562/0209* (2013.01)

(56) References Cited

U.S. PATENT DOCUMENTS

| | | | | |
|---|---|---|---|---|
| 5,083,573 | A * | 1/1992 | Arms | 600/587 |
| 5,161,533 | A * | 11/1992 | Prass et al. | 600/372 |
| 6,735,468 | B2 * | 5/2004 | Treppo et al. | 600/547 |
| 6,915,701 | B1 * | 7/2005 | Tarler | 73/774 |
| 8,190,250 | B2 * | 5/2012 | Moffitt | 600/544 |
| 2008/0262335 | A1 * | 10/2008 | Sun et al. | 600/372 |
| 2009/0048504 | A1 * | 2/2009 | Andino et al. | 600/393 |
| 2011/0282177 | A1 * | 11/2011 | Behrend et al. | 600/386 |
| 2012/0041345 | A1 * | 2/2012 | Rajamani et al. | 600/587 |

OTHER PUBLICATIONS

Fish, et al. "Conduction of electrical current to and through the human body: a review." Eplasty 9 (2009), p. 407-421. Retrieved from <http://www.ncbi.nlm.nih.gov/pmc/articles/PMC2763825/pdf/eplasty09e44.pdf> on May 4, 2015.*

Ahn et al., "Relevance of Collagen Piezoelectricity to "Wolff's Law": A Critical Review", Medical Engineering and Physics; vol. 31, No. 7, Sep. 2009, pp. 733-741.

Anderson et al., "Electrical Properties of Wet Collagen", Nature, vol. 218, Apr. 13, 1968, pp. 166-168.

Barlian et al., "Review: Semiconductor Piezoresistance for Microsystems", Proceedings of the IEEE, vol. 97, Issue 3, Mar. 2009, pp. 513-552.

Benoit et al., "In Vivo Anterior Cruciate Ligament Strain Behaviour During a Rapid Deceleration Movement: Case Report", Knee Surgery, Sports Traumatology, Arthroscopy, vol. 11, No. 5, Sep. 2003, pp. 307-311.

Bergmann et al., "Body-Worn Sensor Design: What do Patients and Clinicians Want?", Annals of Biomedical Engineering, vol. 39, No. 9, Sep. 2011, pp. 2299-2312.

Cawley et al., "Biomechanics of the Lateral Ligaments of the Ankle-An Evaluation of the Effects of Axial Load and Single Plane Motions on Ligament Strain Patterns", Foot and Ankle, vol. 12, No. 2, Oct. 1991, pp. 92-99.

Chen et al., "Effect of Repeated Freezing-Thawing on the Achilles Tendon of Rabbits", Knee Surgery, Sports Traumatology, Arthroscopy, vol. 19, No. 6, Jun. 2011, pp. 1028-1034.

Defrate et al., "The Measurement of the Variation in the Surface Strains of Achilles Tendon Grafts using Imaging Techniques", Journal of Biomechanics, vol. 39, Issue 3, 2006, pp. 399-405.

Erickson et al., "An Invitro Dynamic Evaluation of Prophylactic Knee Braces During Lateral Impact Loading", The American Journal of Sports Medicine, vol. 21, No. 1, Jan.-Feb. 1993, pp. 26-35.

Fleming et al., "In Vivo Measurment of Ligament/Tendon Strains and Forces: A Review", Annals of Biomedical Engineering, vol. 32, No. 3, Mar. 2004, pp. 318-328.

Fukada, Eiichi, "On the Piezoelectric Effect of Silk Fibers", Journal of the Physical Society of Japan, vol. 11, Issue 12, Dec. 1956, pp. 1301A.

Fukada et al., "On the Piezoelectric Effect of Bone", Journal of the Physical Society of Japan, vol. 12, Issue 10, Oct. 1957, pp. 1158-1162.

Fukada et al., "Piezoelectric and Related Properties of Hydrated Collagen", Biophysical Journal, vol. 16, Issue 8, Aug. 1976, pp. 911-918.

Fukada et al., "Piezoelectric Effects in Collagen", Japanese Journal of Applied Physics vol. 3, Issue 2, 1964, pp. 117-121.

Gruverman et al., "Electromechanical Behavior in Biological Systems at the Nanoscale", Scanning Probe Microscopy: Electrical and Electromechanical Phenomena the Nanoscale, Jan. 1, 2007, pp. 615-633.

Hild et al., "Digital Image Correlation: From Displacement Measurement to Identification of Elastic Properties—A Review", Strain, vol. 42, Issue 2, May 2006, pp. 69-80.

Hoffman et al., "Determining the Effect of Hydration Upon the Properties of Ligaments using Pseudo Gaussian Stress Stimuli", Journal of Biomechanics, vol. 35, No. 8, Aug. 2005, pp. 1636-1642.

Huang et al., "Temperature-Dependent Viscoelastic Properties of the Human Supraspinatus Tendon", Journal of Biomechanics, vol. 42, Issue 4, Mar. 11, 2009, pp. 546-549.

Jung et al., "The Effects of Multiple Freeze-Thaw Cycles on the Biomechanical Properties of the Human Bone-Patellar Tendon-Bone Allograft", Journal of Orthopaedic Research, vol. 29, No. 8, Aug. 2011, pp. 1193-1198.

Lichtvvark et al., "In Vivo Mechanical Properties of the Human Achilles Tendon During One-Legged Hopping", The Journal of Experimental Biology, vol. 208, Dec. 2005, pp. 4715-4725.

McDonald et al., "An in Vivo Assessment of Muscular Activity and the Importance of Electrical Phenomena in Bone Remodelling", Journal of Anatomy, vol. 172, Oct. 1990, pp. 165-175.

Minary-Jolandan et al., "Nanoscale Characterization of Isolated Individual Type I Collagen Fibrils: Polarization and Piezoelectricity", Nanotechnology, vol. 20, No. 8, Feb. 25, 2009, 6 pages.

Netto et al., "Effect of Water on Piezoelectricity in Bone and Collagen", Biophysical Journal, vol. 15, No. 6, Jun. 1975, pp. 573-576.

Ravary et al., "Strain and Force Transducers Used in Human and Veterinary Tendon and Ligament Biomechanical Studies", Clinical Biomechanics, vol. 19, No. 5, Jun. 2004, pp. 433-447.

Regling, Gunter, "Conception of a Bioelectromagnetic Signal System via the Collagen Fibril Network; Biochemical Conclusions and Underlying Coherent Mechanism. I. Solid State Effects and Hierarchical Bioelectrical Regulation", vol. 19, No. 2, 2000, pp. 149-161.

Reilly et al., "Arthroscopically Insertable Force Probes in the Rotator Cuff in Vivo", Arthoscopy, vol. 19, No. 2, Feb. 2003, 3 pages.

Smutz et al., "Accuracy of a Video Strain Measurement System", Journal of Biomechanics, vol. 29, No. 6, Jun. 1996, pp. 813-817.

Telega et al., "Piezoelectric Effects in Biological Tissues", Journal of Theoretical and Applied Mechanics, vol. 3, No. 40, 2002, pp. 723-758.

* cited by examiner

APPARATUS METHOD AND SYSTEM FOR MEASURING STRAIN IN BIOLOGICAL TISSUE

RELATED APPLICATIONS

This application claims priority to U.S. Provisional Application 61/633,659 entitled "Use of the Inherent Electrical Properties of Biological Tissue as a Strain Measurement Device" and filed on 15 Feb. 2012 for Christopher R. West and Anton E. Bowden. The foregoing application is incorporated herein by reference in its entirety.

FEDERALLY SPONSORED RESEARCH

This application was made with support from a United States Government grant under Grant Number CMMI-0952758 awarded by the National Science Foundation. The government may have certain rights in this application.

BACKGROUND OF THE INVENTION

1. Field of the Invention

The invention relates to measuring the mechanical properties of biological tissues in general and to measuring strain in tendons and ligaments in particular.

2. Description of the Related Art

A variety of methods exist for measuring the strain of tendons and ligaments such as transducer methods, marker-tracking methods, and medical imaging methods. Transducer based methods typically utilize displacement sensors that are physically attached to the tissue of interest and convert the mechanical energy of displacement (i.e. work) into an electrical signal that can be interpreted by a computer. Examples of such displacement sensors include extensometers, liquid metal strain gauges, Hall effect sensors, and Differential Variable Reluctance Transducers. Marker-tracking based techniques utilize basic continuum mechanics principles to compute the regional strain tensor between groups of "markers" identified on planar or volumetric images of the tissue. These markers can either be externally applied to the tissue or alternatively identified from morphological features.

Marker-tracking techniques have grown more sophisticated and easier to implement in recent years with the development of automatic image digitization and digital image correlation techniques. Medical imaging based strain measurement via ultrasonography and MRI provide non-invasive techniques for measuring in vivo strain, however they can impose a significant cost burden on the researcher.

SUMMARY OF THE INVENTION

Despite the utility of currently available devices, methods and systems for measuring strain in tendons and ligaments, the ability to acquire in situ strain measurements via the electrical properties of the tissue would be a significant advancement over currently available solutions.

As detailed below, an apparatus for in-situ sensing of longitudinal and transverse strain in biological tissue (e.g. tendons and ligaments) includes a set of sensing electrodes that contact biological tissue and enable measurement of an electrical property of the biological tissue along two or more directions. The apparatus also includes a sensing module that senses the electrical property of the biological tissue along the two or more directions to provide a multi-directional measurement of the electrical property that is captured by a logging module. The apparatus may also include a strain estimation module that estimates a longitudinal and transverse strain in biological tissue from the captured measurements and a transmission module that transmits the captured measurements, or the strain estimated therefrom, to a data analysis workstation or the like.

The embodiments described herein provide a variety of advantages. It should be noted that references to features, advantages, or similar language within this specification does not imply that all of the features and advantages that may be realized with the present invention should be, or are in, any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

The aforementioned features and advantages of the present invention will become more fully apparent from the following description and appended claims, or may be learned by the practice of the invention as set forth hereinafter.

BRIEF DESCRIPTION OF THE DRAWINGS

To enable the advantages of the invention to be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE INVENTION

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Some of the functional units described in this specification have been labeled as modules, in order to more particularly emphasize their implementation independence. Others are assumed to be modules. For example, a module or similar unit of functionality may be implemented as a hardware circuit comprising custom VLSI circuits or gate arrays, off-the-shelf semiconductors such as logic chips, transistors, or other discrete components. A module may also be implemented with programmable hardware devices such as field programmable gate arrays, programmable array logic, programmable logic devices or the like.

A module or a set of modules may also be implemented (in whole or in part) as a processor configured with software to perform the specified functionality. An identified module may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, the executable code of a module may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices.

Figure 1:
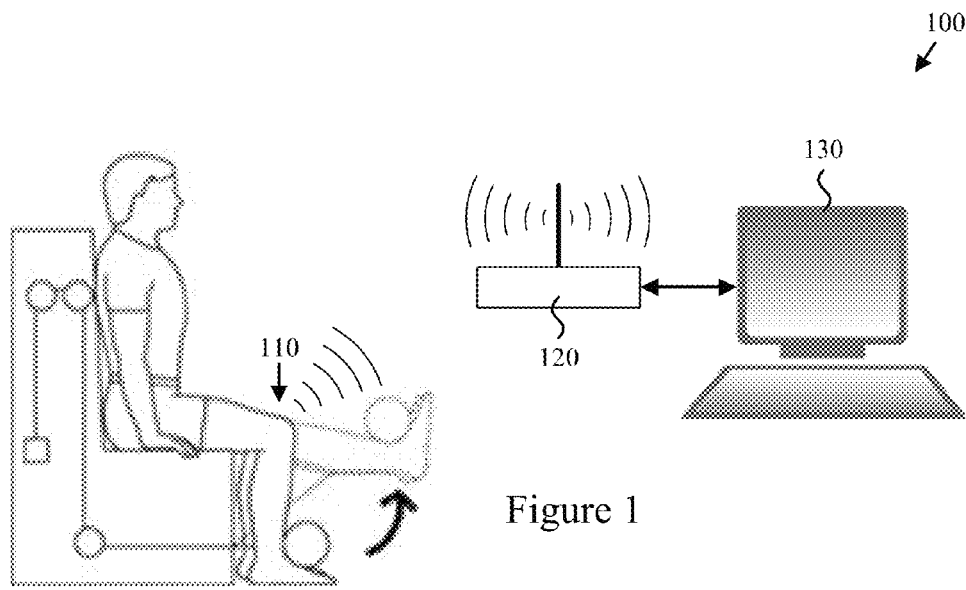
FIG. 1 is a schematic block diagram of a biological tissue strain sensing system in accordance with various embodiments described herein.

FIG. 1 is a schematic block diagram of a biological tissue strain sensing system 100 in accordance with various embodiments described herein. As depicted, the biological tissue strain sensing system 100 includes a biological tissue strain sensing device 110 (hidden from view), a receiver 120 and an analysis workstation 130. The biological tissue strain sensing system 100 facilitates measurement and analysis of strain within biological tissue.

The biological tissue strain sensing device 110 may sense an electrical property of the biological tissue which corresponds to strain on the tissue. In some embodiments, the strain sensing device 110 measures the electrical property along two or more directions to provide multi-directional measurements of the electrical property. The device 110 may also log measurements of the electrical property and transmit them to the receiver 120. In the depicted embodiment, the device 110 includes a wireless transmitter (not shown) and the receiver 120 is a wireless receiver and transmitter.

The data analysis workstation 130 may facilitate viewing and analysis of the measurement data provided by the strain sensing device 110 and received by the receiver 120. In some embodiments, the workstation 130 may also enable a user to control operation of the strain sensing device 110 including activation/deactivation and control of the sampling rate by sending commands to the device 110 via the receiver/transmitter 120.

Figure 2:
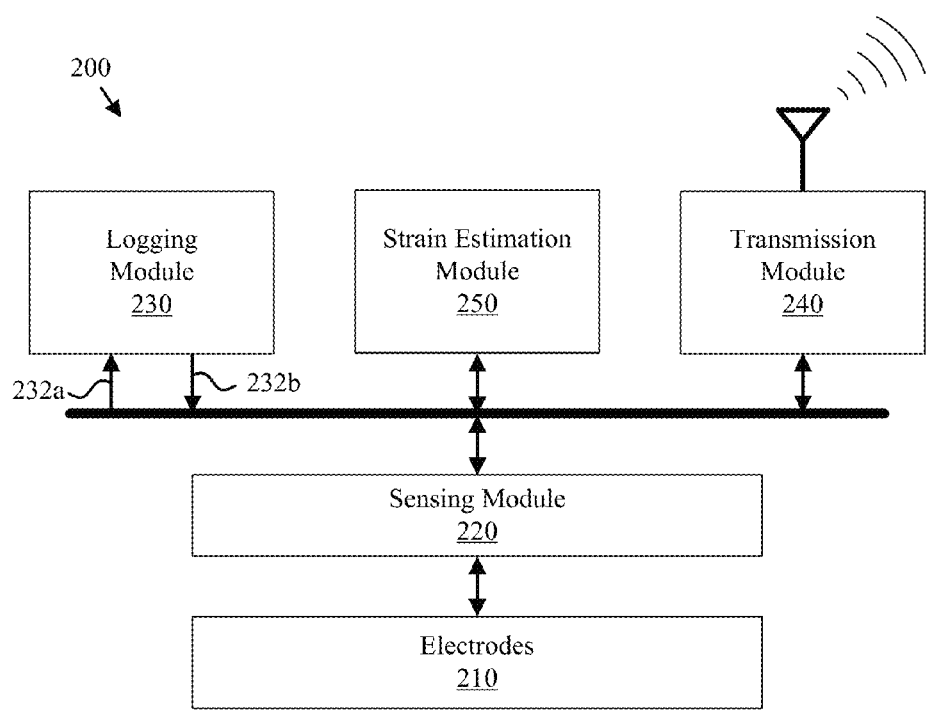
FIG. 2 is a block diagram of a biological tissue strain sensing apparatus in accordance with various embodiments described herein.

FIG. 2 is a block diagram of a biological tissue strain sensing apparatus 200 in accordance with various embodiments described herein. As depicted, the apparatus 200 includes a set of sensing electrodes 210, a sensing module 220, a logging module 230, a transmission module 240 and a strain estimation module 250. The biological tissue strain sensing apparatus 200 enables the measurement of strain within biological tissue.

The sensing electrodes 210 are configured to contact biological tissue and enable measurement of an electrical property of the biological tissue. In some embodiments, the sensing electrodes enable measurement of an electrical property along two or more dimensions to provide multi-directional measurements of the electrical property. In certain embodiments, the sensing electrodes may enable measurement along 3 or more directions.

The sensing module 220 senses the electrical property of the biological tissue along the various directions supported by the sensing electrodes 210. In one embodiment, the electrical property is electrical resistance. In another embodiment the electrical property is electrical potential. In yet another embodiment, the electrical property is electrical current.

One of skill in the art will recognize that the architecture of the apparatus 200 enables electrically connecting the biological tissue as a resistive component (i.e. extension) of a sensing circuit (not shown) within the sensing module 220. In one embodiment, the sensing circuit is a wheatstone bridge that provides high sensitivity to changes in the resistance of the biological tissue.

In some embodiments, the apparatus may be manually aligned with a primary direction of collagen fibers in the biological tissue and sensing of the electrical property occurs along a longitudinal direction and a transverse direction for the collagen fibers to provide a longitudinal measurement and a transverse measurement of the electrical property. In certain embodiments, measurements taken along 3 or more directions are processed by a conversion module (not shown) to automatically determine, independent of the orientation of the apparatus 200, the longitudinal and transverse directions and the corresponding longitudinal and transverse components of the multi-directional measurements. The longitudinal component may correspond to a direction that is substantially parallel to the primary direction of collagen fibers in the biological tissue and the transverse component may correspond to a direction that is substantially perpendicular to the primary direction of collagen fibers in the biological tissue.

Converting to longitudinal and transverse components may involve determining a strongest direction for the electrical property (or variance in the electrical property) and using vector arithmetic to determine the relative strength of the electrical property parallel to and perpendicular to the strongest direction.

The module that converts measurements taken along 3 or more directions to the longitudinal and transverse components may be internal to, or external to, the apparatus 200. In one embodiment, the sensing module 220 functions as the conversion module. In another embodiment, the strain estimation module 250 functions as the conversion module. In yet another embodiment, the conversion module is part of the data analysis workstation 130.

The logging module 230 captures the multi-directional measurements (or the longitudinal and transverse components derived therefrom) that are provided by the sensing module 220 to provide captured measurements. The logging module may have a data port 232a used to store or write the captured measurements, that is separate from a data port 232b used to retrieve or read the captured measurements. In one embodiment, the logging module 230 comprises a FIFO memory that is able to simultaneously capture and provide a sequence of measurements. The transmission module 240 may transmit measurements provided by the logging module 230 to a receiver via a wireless interface or some other communications channel.

In some embodiments, the apparatus 200 includes the strain estimation module 250. In other embodiments, the strain estimation module is part of the data analysis workstation 130. The strain estimation module 250 estimates an actual longitudinal and transverse strain for the biological tissue from captured measurements or longitudinal and transverse components derived therefrom.

One of skill in the art that the modules of the apparatus 200 may be arranged in a variety of configurations that effectively provides the specified functionality.

Figure 3A:
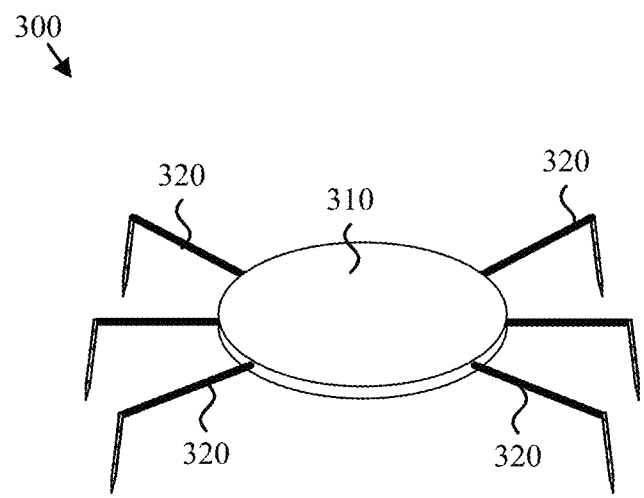
FIG. 3a is a perspective view illustration and FIG. 3b is a side view illustration of a biological tissue strain sensing device 300 in accordance with various embodiments described herein.
Figure 3B:
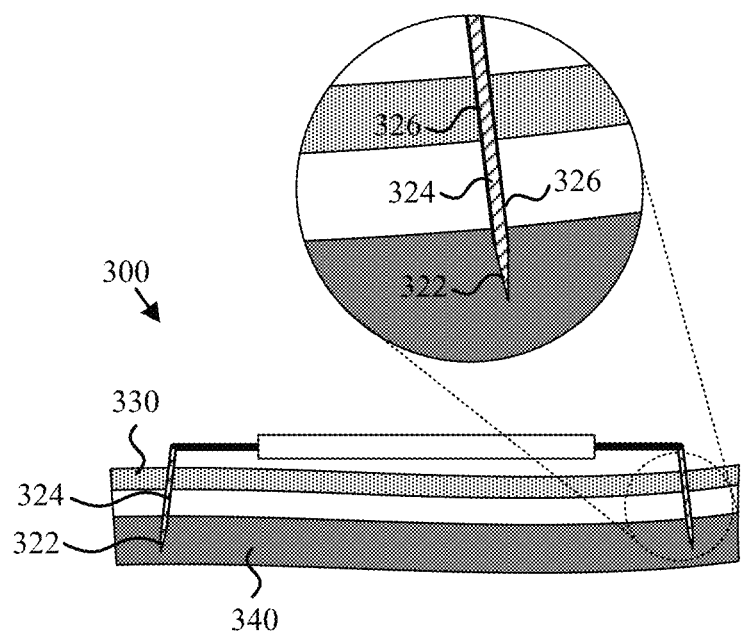

FIG. 3a is a perspective view illustration and FIG. 3b is a side view illustration of a biological tissue strain sensing device 300 in accordance with various embodiments described herein. As depicted, the strain sensing device 300 includes a body 310 and a set of sensing electrodes 320. The strain sensing device 300 is one example of how the biological tissue strain sensing apparatus 200 may be packaged.

The sensing electrodes may be sufficiently stiff to enable penetration of a skin layer 330 yet sufficiently flexible to flex as the skin 330 and a measured layer 340 is stretched, compressed and flexed. Each of the depicted sensing electrodes 320 include an uninsulated tip 322 for penetrating through the skin, a shank 324 configured to provide electrical communication with the tip 322 and an insulating layer 326 for insulating the shank from penetrated skin. The uninsulated tip 322 enables electrical communication with the measured layer 340 and measurement of the electrical properties of that layer.

Figure 4:
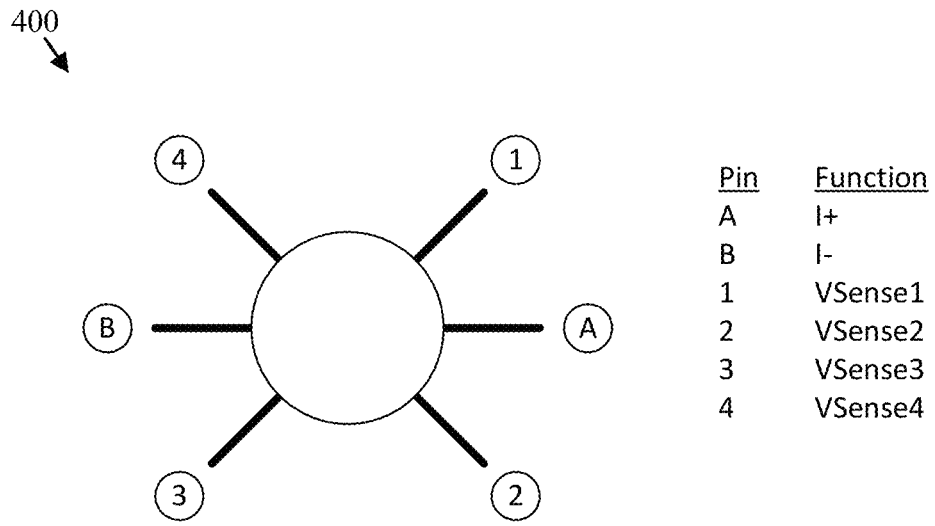
FIG. 4 depicts one example of a sensing configuration in accordance with the biological tissue strain sensing device of FIG. 3.

FIG. 4 depicts one example of a sensing configuration 400 in accordance with the biological tissue strain sensing device of FIG. 3. The depicted configuration include two current electrodes that source and sink a sensing current and four voltage sensing electrodes used to detect a local voltage. By determining a local voltage at each voltage sensing electrode a voltage gradient can be calculated for the biological tissue. Detection of a resting (i.e. quiescent) voltage gradient may enable automatic detection of the primary direction of the collagen fibers. Furthermore, by characterizing the relationship between strain and the voltage gradient during resting and non-resting intervals, detection of the voltage gradient during non-resting intervals can be leveraged to determine the longitudinal and transverse strain on the biological tissue.

Figure 5:
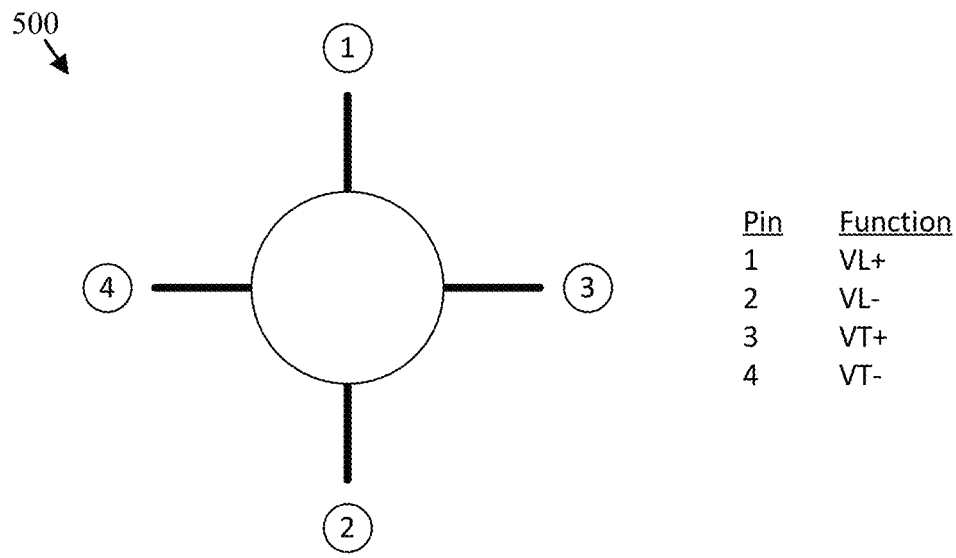
FIG. 5 depicts an alternative example of a sensing configuration of a biological tissue strain sensing device.

FIG. 5 depicts an alternative example of a sensing configuration 500 of a biological tissue strain sensing device. The sensing configuration 500 includes differential longitudinal electrodes VL+ and VL− and differential transverse electrodes VT+ and VT−. The longitudinal electrodes may be manually aligned with a primary direction of collagen fibers in the biological tissue. Each differential electrode pair may be connected to a wheatstone bridge circuit or the like, that senses the current that flows in the biological tissue between the paired electrodes (and therefore the corresponding resistance) in a direction defined by the physical placement of the electrodes.

In some embodiments, the longitudinal and transverse electrodes are time division multiplexed so that a differential voltage is applied to only one electrode pair at any given time. Time division multiplexing may simplify sensing a current that flows between each pair of differential electrodes and calculating a corresponding resistance and strain of the biological tissue in the longitudinal and transverse directions.

Figure 6:
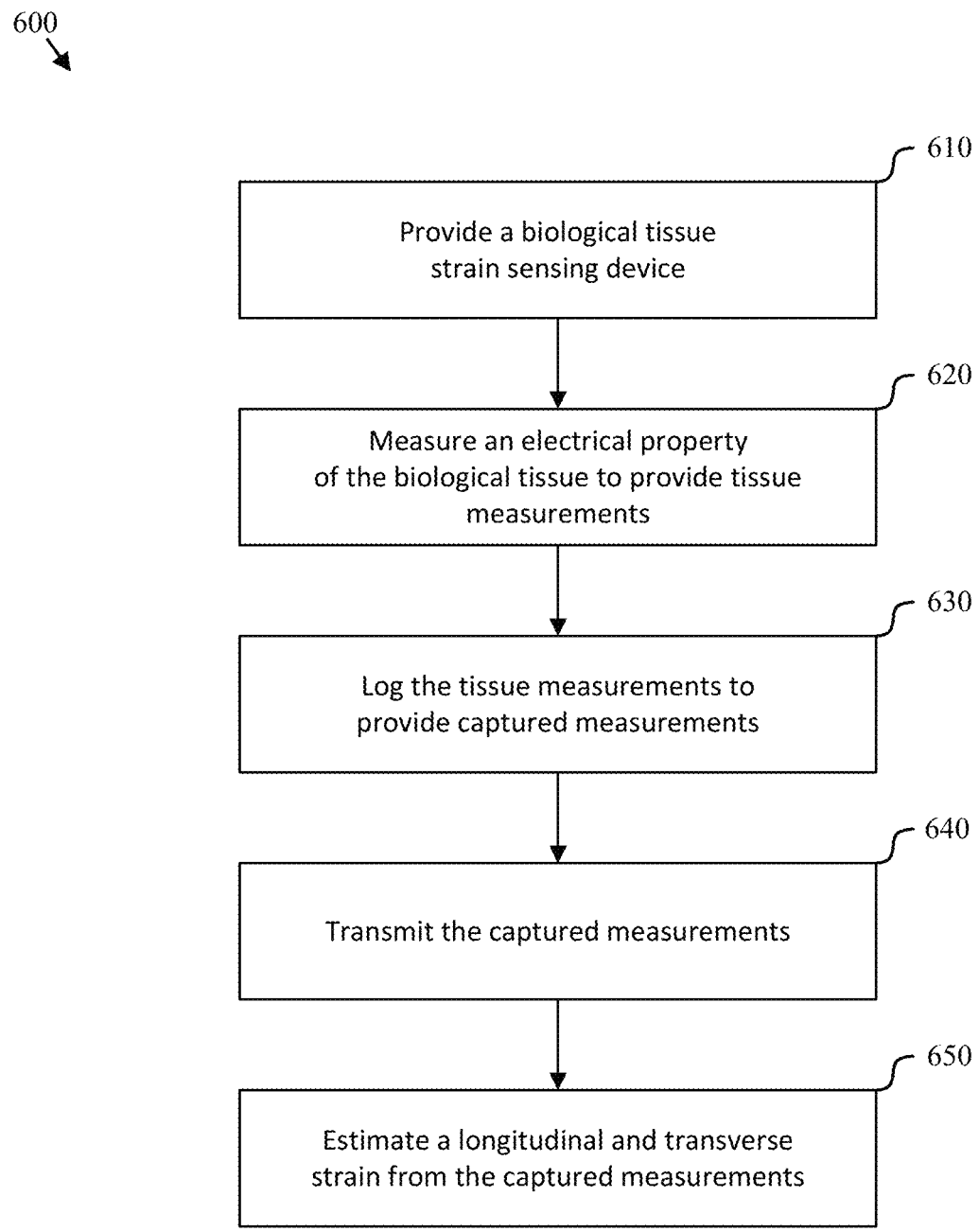
FIG. 6 is a flowchart diagram of a biological tissue strain sensing method in accordance with various embodiments described herein.

FIG. 6 is a flowchart diagram of a biological tissue strain sensing method 600 in accordance with various embodiments described herein. As depicted, the biological tissue strain sensing method 600 includes providing 610 a biological tissue strain sensing device, measuring 620 an electrical property of biological tissue to provide tissue measurements, logging 630 the tissue measurements to provide captured measurements, transmitting 640 the captured measurements and estimating 650 a longitudinal and transverse strain from the captured measurements.

Providing 610 a biological tissue strain sensing device may include providing a device with a set of sensing electrodes that are configured to contact biological tissue and enable measurement of an electrical property of the biological tissue along two or more directions. The device may also include a sensing module configured to sense the electrical property of the biological tissue along the two or more directions via the sensing electrodes.

In certain embodiments, providing 610 may include placing the strain sensing device at an appropriate location and applying pressure to enable the electrodes of the biological tissue strain sensing device to penetrate through a layer of skin and measure the electrical properties of the biological tissue.

Measuring 620 an electrical property of the biological tissue may include measuring along the two or more directions to provide multi-directional measurements of the electrical property of the biological tissue. In certain embodiments, measuring 620 the electrical property may occur along 3 or more directions and a longitudinal component of the electrical property and a transverse component of the electrical property are derived from the multi-directional measurements. The longitudinal component may correspond to a direction that is substantially parallel to a primary direction of collagen fibers in the biological tissue and the transverse component may corresponds to a direction that is substantially perpendicular to the primary direction of collagen fibers in the biological tissue.

Logging 630 the tissue measurements may include storing the measurements (or components derived therefrom) in a transmit buffer or a storage device to provide captured measurements. The captured measurements may correspond to a selected sample rate for the strain sensing device.

Subsequently, transmitting 640 the captured measurements may include reading the captured measurements and providing the captured measurements to a wireless transmitter or similar device to facilitate transmission of the captured measurements to a receiver.

Estimating 650 a longitudinal and transverse strain from the captured measurements may include converting a measured or derived resistance in the longitudinal and transverse directions to an actual strain value. In certain embodiments, a resistance to strain mapping function is used to convert between a measured resistance and an estimated strain. In one embodiment, the resistance to strain mapping function conforms to the equations: $R_L=0.86\epsilon_L$, $R_T=1.59\epsilon_T$ where $R_L$ and $R_T$ represent the longitudinal resistance and the transverse resistance, respectively and $\epsilon_L$ and $\epsilon_T$ represent the longitudinal and transverse strains, respectively.

The present invention facilitates in-situ sensing of longitudinal and transverse strain in biological tissue such as tendons and ligaments. The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus comprising:
a plurality of sensing electrodes that are electrically conductive and configured to contact subcutaneous biological tissue, the plurality of sensing electrodes configured to measure an electrical property of the biological tissue along at least a first direction defined between a first pair of the plurality of sensing electrodes and a second direction defined between a second pair of the plurality of sensing electrodes, the first pair being different from the second pair;
at least one processor; and
a memory storing instructions that, when executed by the at least one processor, causes the apparatus to:
determine a longitudinal component of the electrical property that corresponds to a direction that is substantially parallel to a primary direction of collagen fibers in the biological tissue and a transverse component of the electrical property that corresponds to a direction that is substantially perpendicular to the primary direction of collagen fibers in the biological tissue using the measured electrical property along the first direction and the measured electrical property along the second direction, and
estimate a longitudinal strain in the biological tissue as a function of the longitudinal component and estimate a transverse strain in the biological tissue as a function of the transverse component.

2. The apparatus of claim 1, wherein the electrical property is at least one of electrical resistance, electrical potential and electrical current.

3. The apparatus of claim 1, wherein the plurality of sensing electrodes enable measurement of the electrical property along a third direction defined between a third pair of electrodes, the third pair being different from the first pair and the second pair.

4. The apparatus of claim 1, wherein the plurality o f sensing electrodes electrically connect the biological tissue as a resistive component of a sensing circuit.

5. The apparatus of claim 4, wherein the sensing circuit is a wheatstone bridge.

6. The apparatus of claim 1, further comprising a transmitter for transmitting the multi-directional measurement of the electrical property.

7. The apparatus of claim 6, wherein the transmitter comprises a wireless transmitter.

8. A method comprising:
providing a biological tissue strain sensing device comprising a plurality of sensing electrodes that are electrically conductive and configured to contact biological tissue and to measure an electrical property of the biological tissue in at least a first direction defined between a first pair of the plurality of sensing electrodes and a second direction defined between a second pair of the plurality of sensing electrodes, the first pair being different from the second pair, and a sensing module electrically connected to the plurality of sensing electrodes and configured to sense the electrical property of the biological tissue along the first direction and along the second direction via the plurality of sensing electrodes;
measuring the electrical property of the biological tissue that corresponds to electrical resistance along the first direction and along the second direction to provide a multi- directional measurement of the electrical property;
determining a longitudinal component of the electrical property, wherein the longitudinal component corresponds to a primary direction of collagen fibers in the biological tissue;
determining a transverse component of the electrical property, wherein the transverse component corresponds to a direction that is substantially perpendicular to the primary direction of collagen fibers in the biological tissue; and
estimating a longitudinal strain in the biological tissue and a transverse strain in the biological tissue from the multi-directional measurement, the longitudinal strain being a function of the longitudinal component and the transverse strain being a function of the transverse component.

9. The method of claim 8, further comprising:
repeating the measuring to provide a plurality of multi-directional measurements; and
logging the plurality of multi-directional measurements to provide captured measurements.

10. The method of claim 9, further comprising reading the captured measurements.

11. The method of claim 9, further comprising transmitting the captured measurements.

12. The method of claim 9, wherein the captured measurements correspond to a selected sample rate.

13. The method of claim 8, wherein the electrical property is at least one of electrical resistance, electrical current and electrical potential.

14. The method of claim 8, further comprising penetrating through a layer of skin with the electrodes of the biological tissue strain sensing device to measure the electrical properties of the biological tissue.

15. The method of claim 8, the biological tissue being connected as a resistive component of a sensing circuit within the sensing module.

16. The method of claim 8, wherein the function is a linear function.

17. A system comprising:
a plurality of sensing electrodes that are electrically conductive and configured to contact biological tissue and to measure an electrical property of the biological tissue that corresponds to electrical resistance in at least a first direction defined between a first pair of the plurality of sensing electrodes and a second direction defined between a second pair of the plurality of sensing electrodes, the first pair being different from the second pair,
a wireless transmitter configured to transmit the measured electrical property of the biological tissue in the first direction and the measured electrical property of the biological tissue in the second direction as a multi-directional measurement; and
a workstation configured to receive the multi-directional measurement from the wireless transmitter and estimate a longitudinal strain in the biological tissue in a direction substantially parallel to a primary direction of collagen fibers in the biological tissue and a transverse strain in the biological tissue as a function of the multi-directional measurement.

* * * * *